United States Patent [19]

Gallo

[11] 4,275,163

[45] Jun. 23, 1981

[54] CELLULASE-PRODUCING MICROORGANISM

[75] Inventor: Benedict J. Gallo, Natick, Mass.

[73] Assignee: The United States of America as represented by the Secretary of the Army, Washington, D.C.

[21] Appl. No.: 962,522

[22] Filed: Nov. 20, 1978

[51] Int. Cl.³ ............... C12N 9/42; C12N 15/00; C12R 1/885
[52] U.S. Cl. ............... 435/209; 435/172; 435/254; 435/945
[58] Field of Search ............... 435/209, 254, 945, 172

[56] References Cited

U.S. PATENT DOCUMENTS

| | | | |
|---|---|---|---|
| 3,734,831 | 5/1973 | Hulme | 435/209 |
| 3,972,775 | 8/1976 | Wilke et al. | 435/209 X |

FOREIGN PATENT DOCUMENTS 574471  9/1977  U.S.S.R. ............... 435/209

OTHER PUBLICATIONS

Montenecourt et al., Applied and Environmental Microbiology, vol. 34, pp. 777–782 (Dec. 1977).
Mandels et al., Applied Microbiology, vol. 21, pp. 152–154 (Jan. 1971).
Ladisch et al., Science, vol. 201, pp. 743–745 (Aug. 1978).

*Primary Examiner*—Lionel M. Shapiro
*Attorney, Agent, or Firm*—Nathan Edelberg; Robert P. Gibson; Lawrence E. Labadini

[57] ABSTRACT

A process and a microorganism for synthesizing cellulase enzymes are described. The microorganism is a mutant strain of an Ascomycete fungus capable of synthesizing cellulases. The synthesis of cellulases by the mutant is nonrepressed by glycerol, repressed by glucose but not subject to postrepression lag, and inducible to high levels by lactose. Furthermore, the combination of lactose with xylose elicits maximum cellulase synthesis by the mutant.

7 Claims, 6 Drawing Figures

CELLULASE-PRODUCING MICROORGANISM

The invention described herein may be manufactured, used, and licensed by or for the government for governmental purposes without the payment to us of any royalty thereon.

BACKGROUND AND PRIOR ART

Cellulose is a structural polysaccharide of plants. It is said to be the most abundant organic substance on earth. An estimated $10^{11}$ tons of cellulose are synthesized each year by plants, using photosynthetic energy derived from sunlight. Cellulose is composed essentially of repeating subunits of D-glucose, linked by $\beta$-(1→4)-glycosidic bonds. Total hydrolysis yields D-glucose and partial hydrolysis yields the disaccharide cellobiose, which is 0-$\beta$-D-glucopyranosyl-(1→4)-$\beta$-D-glucopyranose. Therefore, cellulose is a $\beta$-1,4-glucan. Although closely related to starch in composition, the glucose units of cellulose are connected differently than in starch, and this fact profoundly affects their properties. Cellulose is more insoluble than starch and is capable of forming long semicrystalline microfibrils. A closely related polymer, $\beta$-1,3-glucan, can only form amorphous structures.

Cellulose constitutes the major storage form of photosynthesized glucose, and the major component of solar energy converted to biomass. World wide demand for energy and for food supplies are increasing. Cellulose is an attractive raw material for supplying these needs, because of its abundance. The glucose subunits of cellulose can be used in a variety of processes for production of energy on the one hand or for the production of protein on the other. A major difficulty which has stood athwart the advance of cellulose utilization technology has been the difficulty of obtaining glucose in reasonable yield from cellulose at a reasonable cost in terms of energy input, equipment requirements and the like. Enzyme-catalyzed hydrolysis of cellulose is an attractive potential solution to these difficulties. However, the production of adequate amounts of cellulase is dependent upon obtaining a suitable source of large quantities of the enzyme in a reasonably pure state.

Cellulases are found in the digestive tracts of snails, in certain anaerobic bacteria and in other microorganisms, most notably the rumen microorganisms which inhabit digestive tracts of ruminants. A number of fungal species are known to produce cellulase, including fungi of the class Ascomycetes, such as Neurospora and Trichoderma. The fungal systems are perhaps the most attractive because the organisms can be cultured without resort to special growth conditions such as anaerobiosis, and some, at least, are capable of rapid growth.

The fungal system described herein is derived from *Trichoderma reesei*, hereinafter *T. reesei*, an Ascomycete fungus species formerly assigned to the species *Trichoderma viride*. In general, any Ascomycete fungus capable of synthesizing a complete cellulase could be used to derive a strain having similar properties. *T. reesei* is presently preferred because large amounts of cellulase are produced extracellularly. See, Simmons, E. G., *Abstracts of Second International Mycology Congress*, Tampa, Florida, page 618 (1977). The cellulase system produced by this species include an endo-$\beta$-glucanase, exo-$\beta$-glucanase and $\beta$-glucosidase. The first of these enzymes is capable of hydrolyzing $\beta$-glucosidic bonds at mainly internal sites on the cellulose molecule. The second is capable of catalyzing the hydrolytic removal of disaccharide subunits from the ends of the cellulose chain, yielding mainly cellobiose as a product. The $\beta$-glucosidase catalyzes the hydrolysis of cellobiose to glucose. The term cellulase, as used herein, includes all such enzymes including isozymic forms. The cellulase produced by *T. reesei* is found in the growth medium. Synthesis of cellulase by the wild type *T. reesei* is under stringent metabolic and genetic control, in which both induction and repression are observed. The term induction is used herein, as in the art generally, to mean that presence of the substrate to be acted upon by the enzyme, or an analog thereof, is necessary for the synthesis of the enzyme by the organism. Repression is a term used to describe the phenomenon in which the presence of a substance in the growth medium is sufficient to prevent the synthesis of the enzyme. The presence of a repressor substance for a particular enzyme prevents the expression of the gene coding for that enzyme, and the presence of an inducer substance is additionally required for expression of the gene. In cultures of wild type *T. reesei*, cellulose acts as an inducer of cellulase synthesis and its presence is therefore required in the medium to obtain appreciable levels of cellulase synthesis. A number of substances act as repressors, notably glucose and glycerol. The necessary conditions for cellulase synthesis therefore are the presence of cellulose and the near absence of glucose. However, as cellulase is synthesized and cellulose in the medium is degraded, glucose is produced, which may result in the repression of enzyme synthesis. Consequently, the levels of cellulase produced by the wild type strain are never very great. Furthermore, the synthesis of cellulase is characterized by a post repression lag period. Once the growth medium has been exhausted of glucose, synthesis of cellulase, even in the presence of an inducer, does not begin for several hours. Consequently, maximal enzyme production requires mutational alteration of the wild type strain, to modify the stringent controls normally limiting the rate of expression of the cellulase genes.

SUMMARY OF THE INVENTION

The present invention concerns a microorganism having useful properties for the production of cellulase enzymes. The microorganism is a strain of *T. reesei*, designated MCG77, which is the end result of a plurality of mutation and selection steps, outlined diagrammatically in FIG. 1. Also shown in FIG. 1 is the mutant strain, NG14, as reported by Montenecourt, B.S. and Eveleigh, D.E., *Appl. and Environ. Microbiol.* 34, 777 (1977).

*T. reesei* MCG77 has the following significant properties: The organism produces cellulase extracellulary at a high rate. Cellulase production is repressed by glucose, but there is no post repression lag in cellulase production following exhaustion of glucose or transfer to a glucose-free medium. Cellulase synthesis is not sensitive to glycerol repression. In addition to cellulose, synthesis of the enzymes is inducible by soluble substances such as lactose. Xylose potentiates lactose-induced cellulase synthesis. The organism is genetically haploid when grown in laboratory culture conditions.

The foregoing attributes provide a variety of significant operating advantages for the production of cellulase by cultures of *T. reesei* MCG77. Rapid post repression recovery makes it possible to synthesize large quantities of cellulase at a rapid rate after growth on glucose to achieve a desired biomass. Lack of glycerol repression makes it possible to synthesize cellulase in continuous cultures in the presence of an inducer. Glycerol is a relatively cheap carbon source for growth of MCG77 since it is a byproduct of ethanol fermentation. The ability to induce with a soluble sugar or combination of sugars simplifies the overall fermentation process, making it possible to use simpler equipment and reducing the overall energy requirement. In general, since the organism reproduces as a haploid organism under current culture conditions, it is exactly reproducible from one generation to the next, without genetic variation.

*Trichoderma reesei* MCG77 was placed on deposit December 20, 1977 in the culture collection of the Northern Regional Research Center of the U.S. Department of Agriculture, 1815 North University Street, Peoria, Illinois, 61604. The strain is designated NRRL 11,236.

DETAILED DESCRIPTION OF THE INVENTION

Strains QM9414 and NG14 were maintained on Potato Dextrose agar slants. MGC77 was maintained on agar slants containing Vogels salts supplemented with biotin, 0.00005% (w/v) and cellulose 1.25%–2.25% (w/v). See Difco Manual, 9th Edition, Difco Laboratories Inc., Detroit, (1953). Some experiments were carried out with 10 liter submerged cultures using a commercial fermenter, New Brunswick Scientific Company, Model MA114. The growth medium was a basic salt medium, described by Mandels, M., *Symposium On Cellulose As A Chemical and Energy Source,* Biotechnol.-Bioeng.Symp. No. 5, R. Wilke, Ed., Wiley-Interscience, New York, page 681 (1975), except that urea was omitted and proteose peptone, 0.1% (w/v) and Tween 80, 0.1% (w/v), Trademark, ICI United States Inc., Wilmington, Delaware, were added. Inoculum cultures were started with conidia from slants, grown for three days in the indicated medium supplemented with cellulose, 0.75% (w/v) and glucose, 0.75% (w/v). The fermenters were inoculated with either a 10% or 20% (v/v) inoculum. Temperature, dissolved oxygen and pH were controlled and continuously recorded during the experiments. The pH was initially allowed to fall from 5.0 to 3.0 and controlled at 3.0 by addition of 2 N $NH_4OH$, as needed. Temperature was maintained at 27°–28° C. Aeration was set at 2 liters/min flow at 7 psig pressure, with agitation varied between 300 rpm to 500 rpm.

Cellulase activity was measured with carboxymethylcellulose (CMC) or filter paper (FP) as substrate, as described in Andreotti, R. E., et al., Proceedings Bioconversion Symp., I.I.T., Delhi, page 249 (1977). One unit of activity is the amount of enzyme catalyzing release of one micromole of glucose per minute. Cellulase activity with cotton as a substrate is expressed as milligrams of reducing sugar (glucose) produced when 1 ml of culture filtrate acts on 50 mg of cotton for 24 hours at pH 4.8 at 50° C. in a unshaken test tube. $\beta$-glucosidase was measured in international units (micromoles glucose released per minute) using Salicin, as described by Mandels, M., et al., Biotechnol.Bioeng-.Symp. No. 6, Wiley-Interscience, New York, page 21 (1976). Filter paper (FP) and cotton are used as substrates to measure the activity of the total cellulase system. Carboxymethyl cellulose (CMC) is used as a substrate to measure the activity of endo-$\beta$-glucanase.

Figure 1:
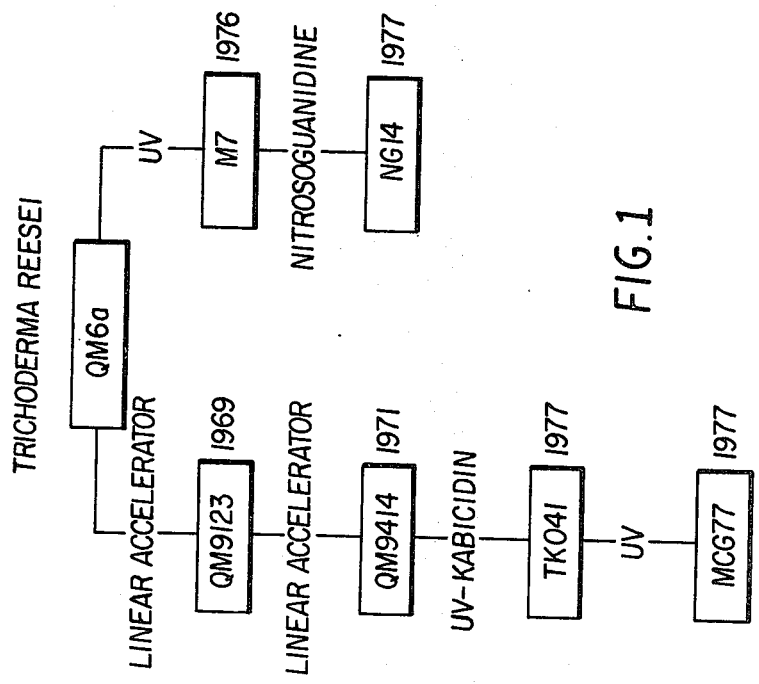

Strain MCG77 was derived from wild type *T. reesei* in a series of steps involving mutagenesis followed by selection, as outlined in FIG. 1. The strains QM9123 and QM9414 have been described previously, Mandels, M. et al., *Applied Microbiology* 21, 152 (1971). Strain TKO41 was produced by ultraviolet light mutagenesis and selected by ability to survive Kabicidin treatment. Strain MCG77 was produced by subjecting strain TKO41 to UV mutagenesis and selected on the basis of its ability to clear cellulose on an agar plate containing 8% (w/v) glycerol and was further selected for freedom from glycerol repression and submerged culture. Strain NG14 and its precursor have been described previously, Montenecourt, B. S. and Eveleigh, D. E., *Appl. and Environ. Microbiol.* 34, 77 (1977). Under the described growth conditions, the production of cellulase by Trichoderma strains typically occurs subsequent to the period of most active growth. During the first fifty hours, the pH is allowed to fall rapidly and biomass reaches a maximum, but only small amounts of cellulase are produced. Most cellulase production occurs during the second fifty hour period as residual cellulose is being consumed, and biomass remains steady or decreases slowly. Attempts to prolong the enzyme production phase by adding more cellulose later in the fermentation have been only modestly successful. Use of a highly crystalline cellulose such as fibrous cotton prolongs the production phase because the substrate is more slowly consumed.

In most Ascomycete fungi, including Neurospora and Trichoderma, and in all strains of *T. reesei* including MCG77, glucose represses cellulase production. In all known *T. reesei* strains except MCG77, there is a substantial post repression lag period following glucose exhaustion during which cellulase production continues at a low level. In fact, in the case of QM9414, the recovery from glucose repression is not complete and therefore this strain produces less cellulase when grown on glucose then when grown on cellulose. The ability of MCG77 to recover rapidly and completely from glucose repression has a significant practical advantage in that it permits rapid buildup of biomass by growth on glucose followed by rapid production of cellulase upon transfer to a cellulose medium lacking glucose. With this growth regimen, maximal cellulase production is obtained in significantly shortened times.

As previously stated, strain MCG77 was selected to be free of glycerol repression. This property is advantageous from an industrial standpoint since it enables cultures of the organism to produce cellulase under conditions which are nonlimiting with respect to metabolic energy. The ability to continue making cellulase in the presence of glycerol, with cellulose as an inducer, suggests that the mutation in MCG77 is not simply to render the organism unresponsive to glucose but rather to alter the quality of its response.

Another salient feature of MCG77 is its inducibility by lactose. Normal inducers of cellulase synthesis in wild type *T. reesei* are cellulose itself and cellobiose. The latter is expensive compared to cellulose and suffers along with cellulose from the disadvantage that induced cellulase acts upon the inducer substance to yield glucose, a repressor. The ability to recognize inducer analogs such as lactose offers a number of distinctive methodological advantages. The ability to work with soluble materials in the fermentation reduces engineering problems associated with insoluble substances in a fermentation. There will be no loss of cellulase due to adsorption on the surface of residual cellulose. Fermenter volume is used more efficiently, since a greater proportion can be devoted to fungal biomass and less energy is required to agitate and aerate the fermenter. In addition, the amount of inducer can be increased since there is no limitation imposed by bulk as there is with cellulose. More significantly, lactose is a major constituent of whey, which is waste byproduct of the cheese making industry. A large supply of an inexpensive byproduct is therefore available for low cost production of cellulase. In this regard, the phenomenon that xylose, which is not in itself an inducer, potentiates the inducing affect of lactose, takes on added significance. Xylose is produced in large amounts in the pretreatment of such plant celluloses as straw and corn stover. At present, so much xylose is produced in such processes that the price is very low. The combined use of lactose with xylose results in nearly double the cellulase production obtained with cellulose-induced MCG77 in shake flask cultures and provides, in addition, all of the foregoing advantages of soluble inducers. Furthermore, the ability to synthesize cellulase in the absence of cellulose eliminates one of the more serious difficulties in obtaining high yields, the fact that the products of cellulose hydrolysis, cellobiose and glucose, repress enzyme synthesis. Therefore, cellulase production with *T. reesei* MCG77 permits maximal cellulase synthesis in a cellulose-free medium. Details of the growth and regulation characteristics of MCG77 are given in the examples.

Strain MCG77 is further characterized by poor growth and apparent failure to conidiate on potato dextrose agar medium. In addition, the strain produces a unique pinkish broth after 6 to 8 days growth in submerged culture on medium 4577MP. This medium has the following composition, expressed in weight percent of volume: $KH_2PO_4$, 1.5%; $MgSO_4.7H_2O$, 0.03%; $(NH_7)_2HPO_4$, 0.28%; $CaCl_2.2H_2O$, 0.03%; Urea, 0.06%; Proteose Peptone, 0.1%; Biotin, 0.00005%; Mandels trace elements, 1 ml (See, Mandels, M., supra); and a carbon source, usually 1% cellulose. Strain MCG77 shows little, if any, growth in the presence of Kabicidin, 100 mg/ml, after mycelial transfer to medium containing Kabicidin.

In general, strain MCG77 may be grown on any medium suitable for growth of *T. reesei* strains. The medium pH should be maintained at pH 3 or higher.

EXAMPLE 1

Figure 2:
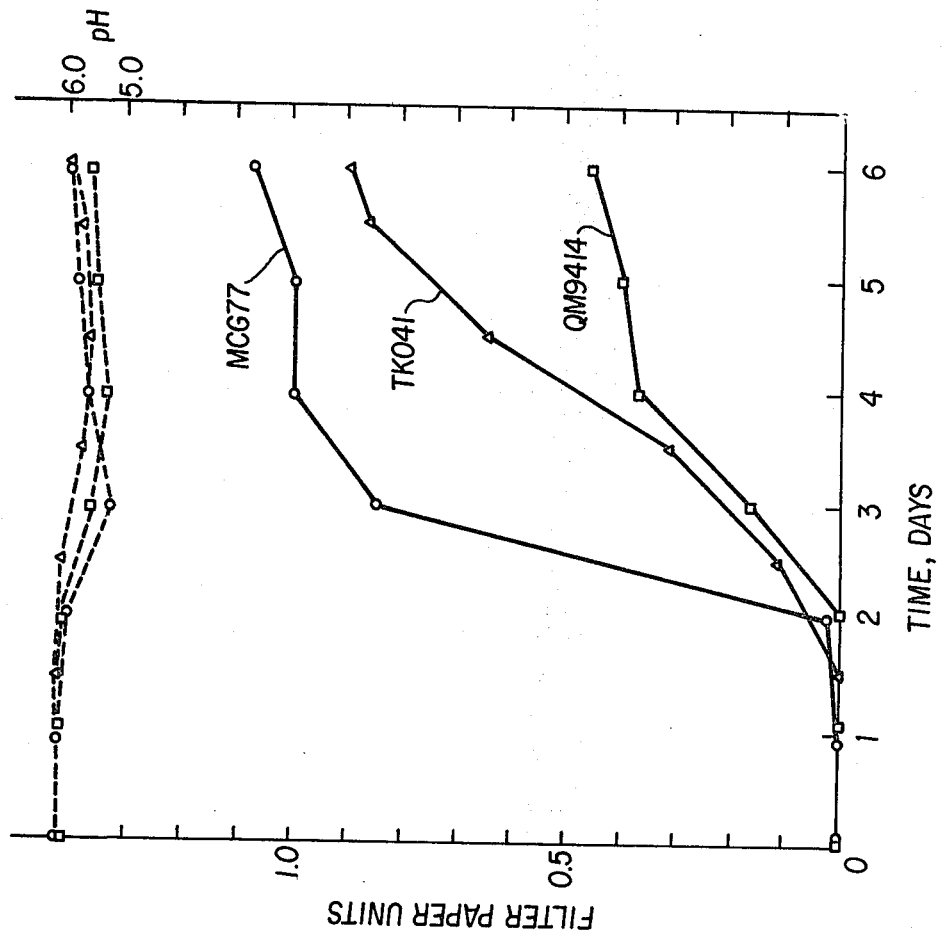

Cellulase production in *T. reesei* strains. Each strain was grown in a Fernbach vessel (shake flask) containing one liter of the previously described medium 45 77 MP supplemented with 1% (w/v) cellulose and buffered with 1.5% (w/v) $KH_2PO_4$. The cultures were incubated at 28° C. on a rotary shaker. At the indicated times, 5 ml alliquots were removed from the culture and assayed for pH and cellulase activity in the supernatant. The results for strains QM9414, TKO41, and MCG77 are shown in FIG. 2. In all strains, the onset of cellulase production was delayed for approximately two days, during which time biomass increased (data not shown). Once cellulase synthesis began, strain MCG77 synthesized cellulase at a more rapid rate and to a greater extent than the other strains.

EXAMPLE 2

Figure 3:
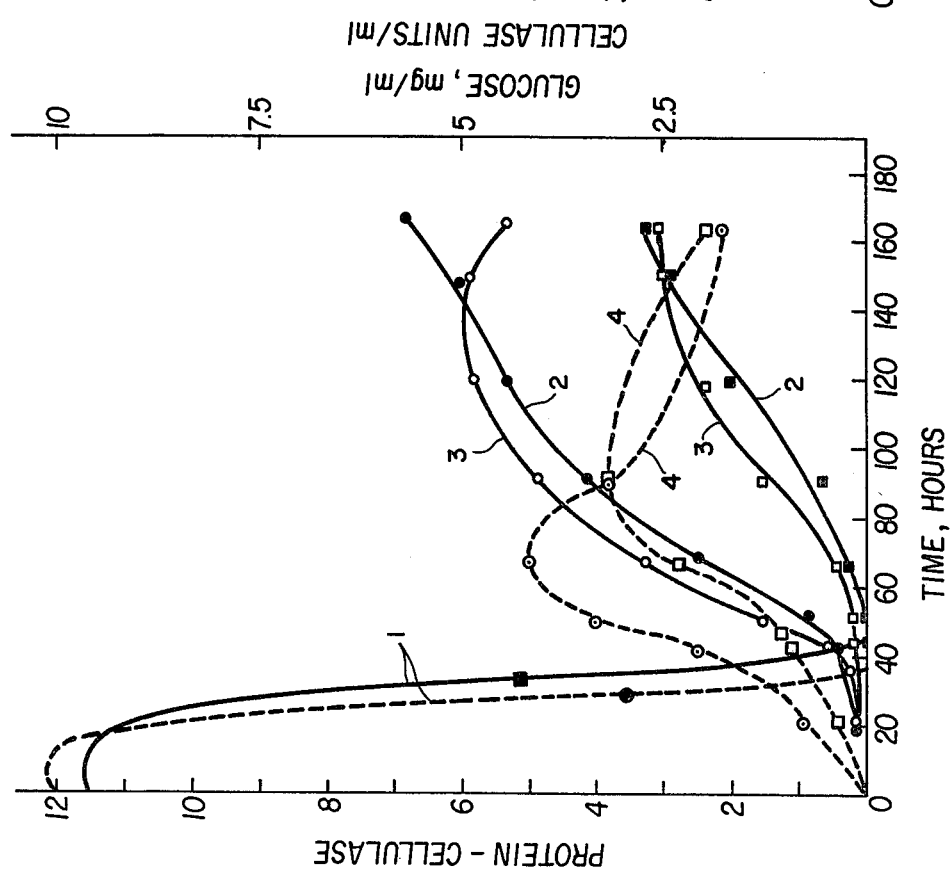

Growth, cellulase production and response to glucose exhaustion. FIG. 3 shows the results of a similar growth experiment in which, in addition to cellulase production, filter paper cellulase units/ml (FP), mycelial protein (M Pr), soluble protein (S Pr) and glucose in the medium (G) were measured as a function of time. Strain MCG77 was compared with QM9414. The cultures were grown essentially as described in Example 1 except the medium contained 1% glucose initially and 2% ball milled 200 mesh spruce wood pulp, Brown Company, Berlin, New Hampshire. Mycelial and soluble protein were measured by the method of Lowry, O. H., et al., *Biochem.* 193, 265 (1951). In FIG. 3, values obtained with the strain MCG77 are represented by circles and those for QM9414 are represented by squares. The curves identified as 1 represent glucose consumption. Curves 2 represent FP assay. Curves 3 represent soluble protein and curves 4 represent mycelial protein. It can be seen that the onset of cellulase synthesis coincided generally with the exhaustion of glucose from the medium in both strains, however, with MCG77, cellulase synthesis commenced immediately and rapidly. With QM9414, cellulase synthesis was delayed due to post repression lag and the rate of synthesis was significantly lower than with MCG77. With MCG77, substantial amounts of cellulase were synthesized within 10 hours of glucose exhaustion. In both strains, the rate of synthesis of soluble protein in the medium and of cellulase were essentially parallel.

EXAMPLE 3

Figure 4:
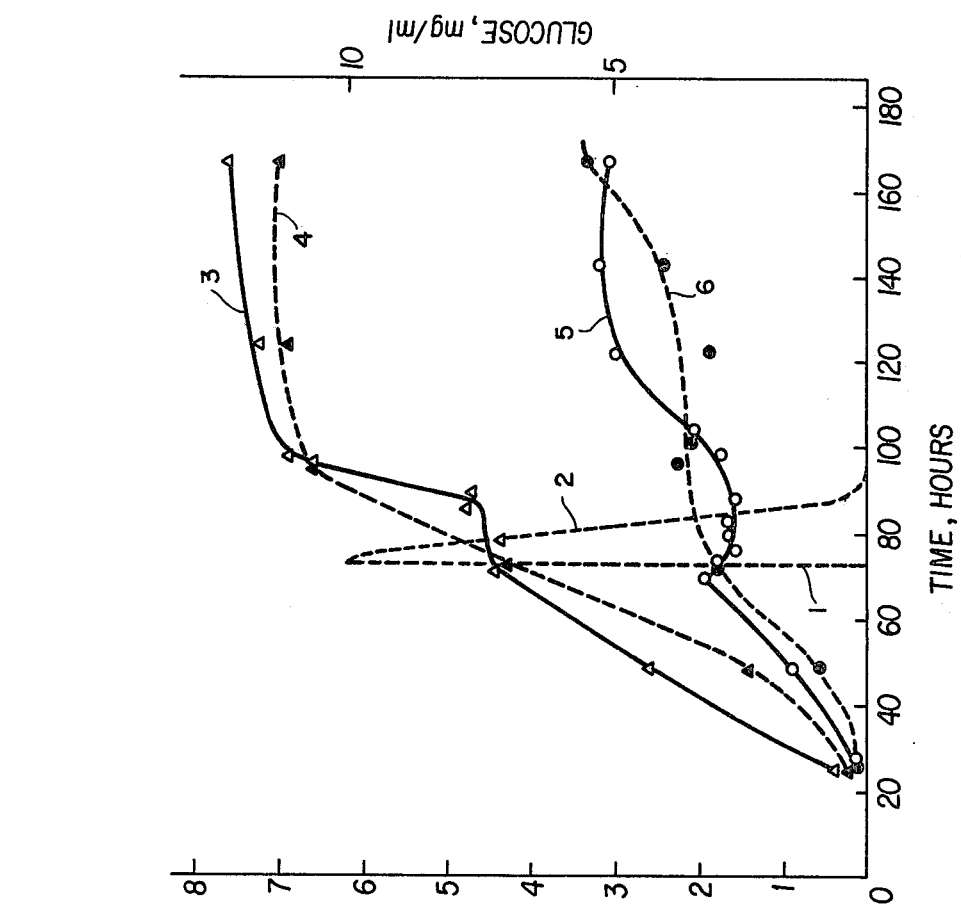

Glucose pulse experiment. In order to further demonstrate glucose repression and lack of post repression lag in MCG77, a glucose pulse was administered to a culture in the cellulase synthesis phase of growth. A 10% (v/v) inoculum of mycelium grown on 1% (w/v) glucose was used to initiate growth in a fermenter containing cellulose as a carbon source in the form of 1.5% (w/v) 40 mesh sprucewood pulp (Brown Company, Berlin, New Hampshire) further processed by being passed twice through a roll mill for one minute at 20 mil gap, and 0.5% (w/v) cotton also twice roll milled at 10 mil gap. See, Tassinari, T. and Macy, C., *Biotechnol. Bioeng.* 19, 1321 (1970). Results of two fermentations run in parallel, one having a 1% glucose pulse added at 74 hours, the other unpulsed, are shown in FIG. 4. The curve identified as 1 represents the glucose pulse and curve 2 represents glucose consumption. Curve 3 is glucose pulsed, CMC assay and curve 4 is non-pulsed CMC assay. Curve 5 is glucose pulsed, FP assay and curve 6 is non-pulsed FP assay. Cellulase was assayed using filter paper (FP) as substrate and carboxymethylcellulose (CMC) as substrate. It can be seen that even after cellulase synthesis had commenced, glucose repressed further synthesis. However, once the glucose in the medium was exhausted, cellulase synthesis began again, without a substantial post repression lag. Substantial amounts of cellulase were synthesized within 10 hours of glucose exhaustion. The amount of cellulase ultimately produced in the glucose-pulsed fermenter was a high or higher than that of the control.

EXAMPLE 4

Figure 5:
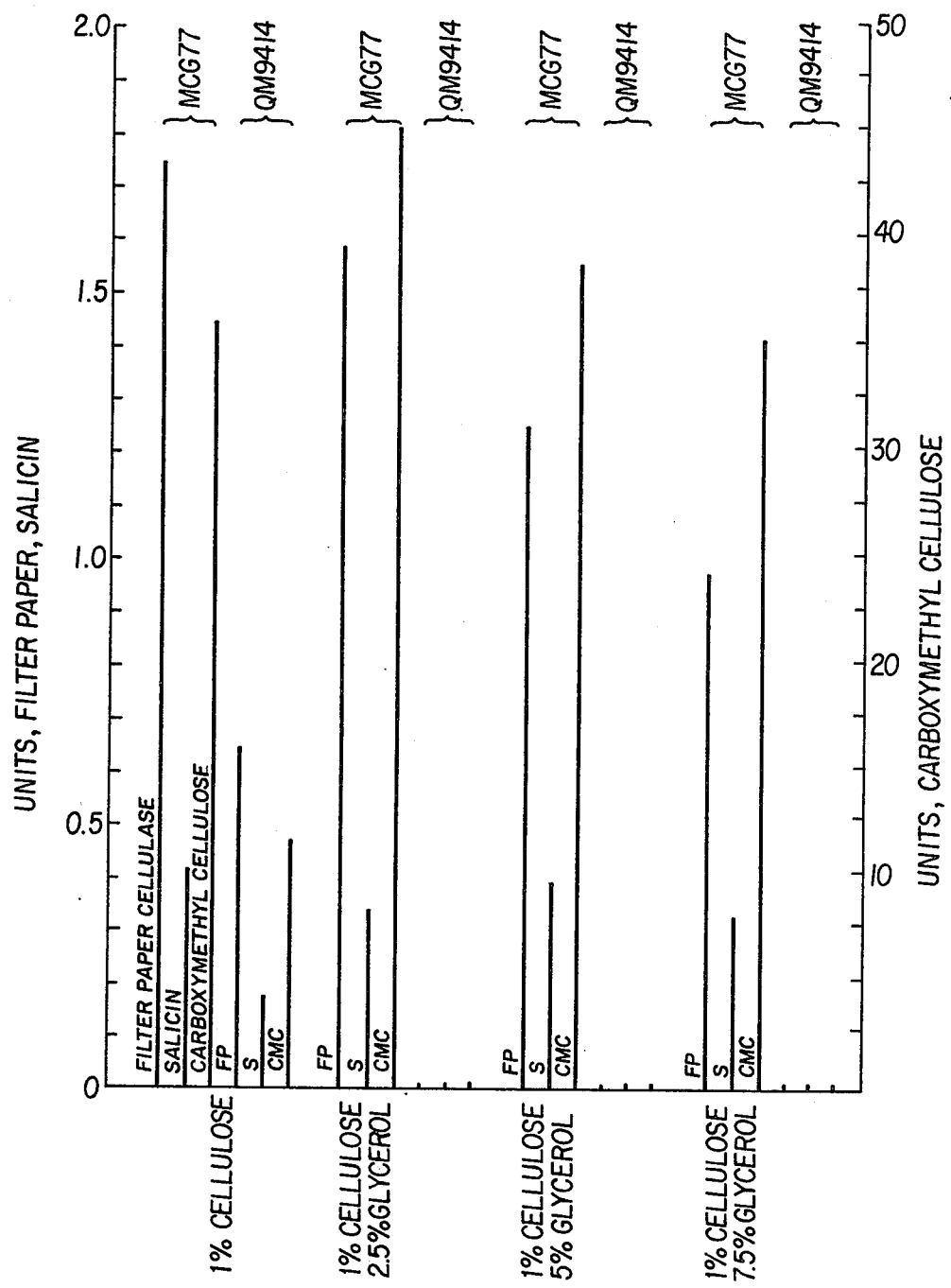

Effects of glycerol on cellulase synthesis by MCG77 and QM9414. The two strains were grown in shaker flasks containing 30 mls of medium as described previously, containing either 1% (w/v) cellulose or cellulose glycerol mixtures as indicated in FIG. 5. In these experiments the media were buffered with 1.5% (w/v) $KH_2PO_4$ to maintain pH greater than 3.0. Duplicate cultures of strain QM9414 and triplicate cultures of strain MCG77 were grown on a reciprocal shaker for 162 hours at 28° C. Cellulase activity in the supernatant was then determined using filter paper (FP), Salicin (S) or carboxymethylcellulose (CMC) as substrates. The average values for each assay were plotted. Cellulase production was essentially completely repressed in QM9414 by the presence of 2.5% glycerol. On the other hand, cellulose was synthesized by MCG77 and in significantly greater amounts than QM9414 in the absence of glycerol. The addition of glycerol produced only a modest decrease in the amount of enzyme synthesized. Even in the presence of 7.5% (w/v) glycerol, substantially more cellulase was synthesized by MCG77 than by non-repressed QM9414. Strain MCG77 can metabolize glycerol and is able to synthesize cellulase at the same time that glycerol is being consumed (data not shown). The response of MCG77 to glycerol is highly significant from a practical standpoint. Cellulose hydrolysis may be coupled with ethanol fermentation for the large scale production of ethanol. Glycerol formed as a byproduct during ethanol production could be recycled for growth and production of biomass of the fungus used to produce more cellulase.

EXAMPLE 5

Figure 6:
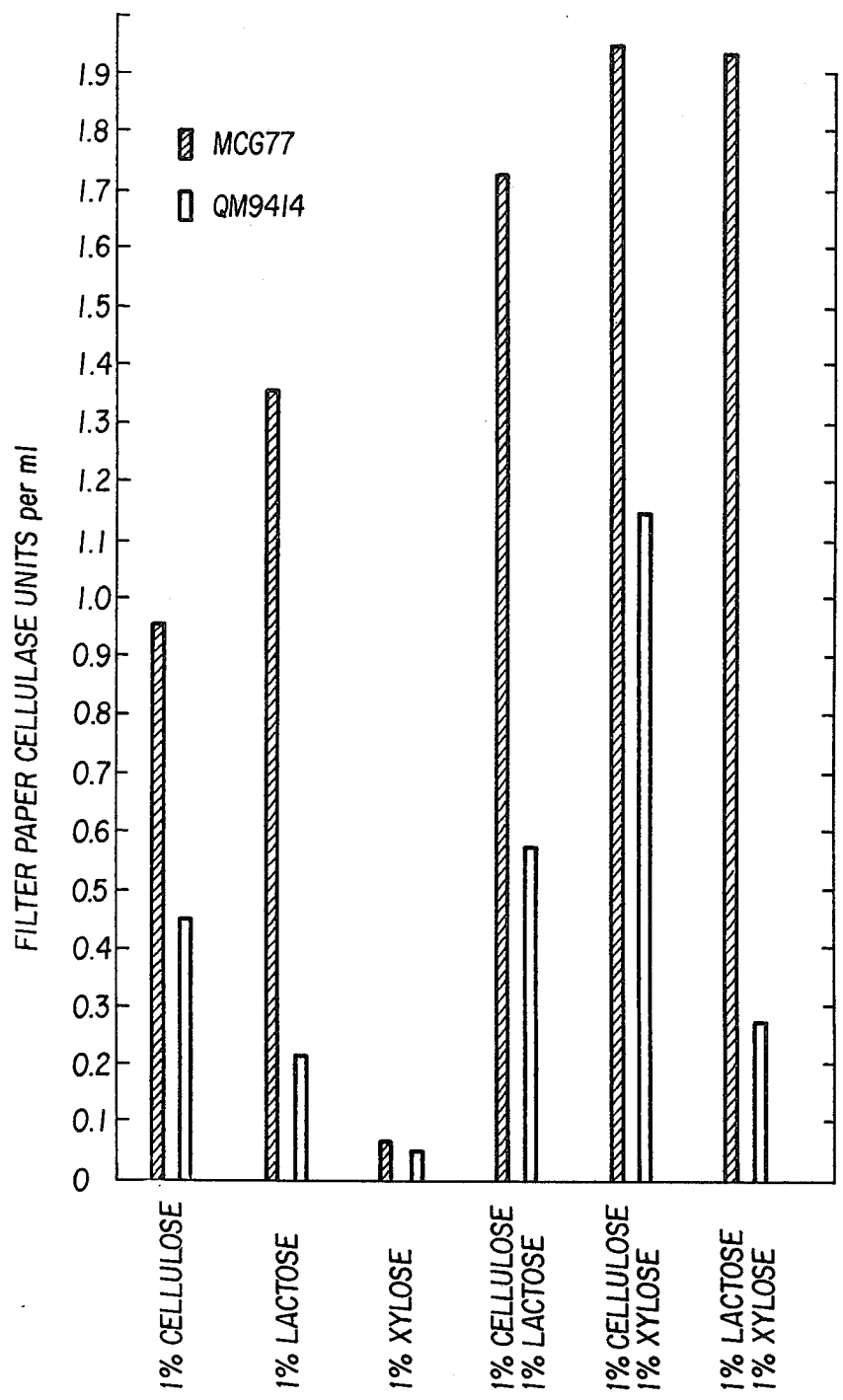

Effects of lactose and xylose on the induction of cellulase synthesis. FIG. 6 shows the amounts of total cellulase produced in a six-day incubation in the presence of the indicated substances as inducers, comparing strain MCG77 with QM9414. The growth medium is medium 4577 MP modified to contain Urea, 0.08%; $KH_2PO_4$, 1.25%; and $(NH_4)_2HPO_4$, 0.53%. As previously observed, cellulase production induced by cellulose alone was substantially greater with MCG77 than with QM9414. Surprisingly, cellulase synthesis by MCG77 was inducible by lactose, which appeared even more effective then cellulose. Xylose did not act as an inducer of either strain. However, with MCG77, xylose strongly potentiated the induction by either cellulose or lactose. Maximum cellulase production, substantially greater than that obtained by cellulose induction was observed when xylose was present in combination with cellulose or lactose as an inducer. The property of being inducible for maximum cellulase synthesis by the combination of two soluble sugars, lactose and xylose, appears to be unique to strain MCG77.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims. In particular, mutations altering quantitative aspects of growth or cellulase synthesis behavior, such as may be obtained by the altered function of any modifier genes, are contemplated within the scope of the present invention.

What is claimed is:

1. A biologically pure culture of *Trichoderma reesei* strain MCG77, said culture having the capability to synthesize cellulase enzymes, the synthesis of the cellulases being nonrepressed by glycerol, repressed by glucose but not subject to post repression lag, and inducible by lactose, the lactose induction being potentiated by xylose, whereby maximum cellulose synthesis is elicited by the presence of lactose and xylose in combination in the culture medium, the organism being genetically haploid under laboratory culture conditions.

2. A process for producing enzymes capable of catalyzing the hydrolysis of cellulose comprising:
    inoculating a growth medium with a microorganism comprising a mutant strain of *Trichoderma reesei* having the capability to synthesize cellulase enzymes, the synthesis of the cellulase enzymes being nonrepressed by glycerol, repressed by glucose but not subject to post repression lag, and inducible by lactose, the lactose induction being potentiated by xylose, and inducible by cellulose, the cellulose induction being potentiated by xylose, said growth medium containing an inducer of cellulase synthesis, and
    incubating the microorganism for a time sufficient to obtain cellulase synthesis.

3. The process of claim 1 wherein the mutant strain of *Trichoderma reesi* is MCG77.

4. The process of claim 1 wherein the inducer of cellulase synthesis is lactose.

5. The process of claim 1 wherein the growth medium contains xylose.

6. The process of claim 1 wherein the growth medium contains glycerol.

7. The process of claim 4 wherein the growth medium contains xylose.

* * * * *

UNITED STATES PATENT OFFICE
CERTIFICATE OF CORRECTION

PATENT NO. : 4,275,163
DATED : June 23, 1981
INVENTOR(S) : Benedict J. Gallo

It is certified that error appears in the above-identified patent and that said Letters Patent are hereby corrected as shown below:

In claim 1, line 7, "cellulose" should read --cellulase--;

In claims 3-6, lines 1, "1" should read --2--.

Signed and Sealed this

Third Day of August 1982

[SEAL]

Attest:

Attesting Officer

GERALD J. MOSSINGHOFF

Commissioner of Patents and Trademarks